US012778455B2

(12) United States Patent
Deixler et al.

(10) Patent No.: US 12,778,455 B2
(45) Date of Patent: Nov. 3, 2026

(54) FALL DETECTION SYSTEM FOR FALL DETECTION OF A PERSON, METHOD FOR FALL DETECTION OF A PERSON AND A COMPUTER PROGRAM PRODUCT FOR FALL DETECTION OF A PERSON

(71) Applicant: SIGNIFY HOLDING B.V., Eindhoven (NL)

(72) Inventors: Peter Deixler, Arlington, MA (US); Alexander Henricus Waltherus Van Eeuwijk, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 19/110,884

(22) PCT Filed: Sep. 5, 2023

(86) PCT No.: PCT/EP2023/074242
§ 371 (c)(1),
(2) Date: Mar. 12, 2025

(87) PCT Pub. No.: WO2024/056446
PCT Pub. Date: Mar. 21, 2024

(65) Prior Publication Data

US 2026/0076587 A1 Mar. 19, 2026

Related U.S. Application Data

(60) Provisional application No. 63/405,557, filed on Sep. 12, 2022.

(30) Foreign Application Priority Data

Sep. 19, 2022 (EP) .................................... 22196264

(51) Int. Cl.
*A61B 5/00* (2006.01)
*A61B 5/05* (2021.01)
*A61B 5/11* (2006.01)

(52) U.S. Cl.
CPC .............. *A61B 5/1117* (2013.01); *A61B 5/05* (2013.01); *A61B 5/7275* (2013.01);
(Continued)

(58) Field of Classification Search
CPC ....... A61B 5/1117; A61B 5/05; A61B 5/7275; A61B 2503/08; A61B 2505/07; A61B 2562/0204
See application file for complete search history.

(56) References Cited

U.S. PATENT DOCUMENTS

2016/0220153 A1 8/2016 Annegarn et al.
2019/0175074 A1* 6/2019 Zhang ...................... H04B 7/22
(Continued)

FOREIGN PATENT DOCUMENTS

CN 107749143 * 2/2018 ........... G08B 21/043
WO 2021050966 A1 3/2021
(Continued)

OTHER PUBLICATIONS

URL: https://www.cdc.gov/steadi/pdf/steadi-brochure-postural-hypotension-508.pdf, "Postural Hypotension, What It Is & How to Mange It," Centers for Disease Control and Prevention, Last Retrieved Mar. 10, 2025 (2 Pages).
(Continued)

*Primary Examiner* — Joel Lamprecht

(57) ABSTRACT

A fall detection system for performing a fall detection of a person (30) is provided and comprises at least one motion and/or presence detector (1) to detect a motion or a presence of a person (30). The at least one motion and/or presence detector (1) are operated in at least a first operating mode
(Continued)

with first operating parameters or a second operating mode with second operating parameters. A fall detector (200) is provided to detect a position or a presence of the person (30) based on sensing signal from at least one motion and/or presence detector (1). The fall detector (200) detects a dwell time a person sitting or lying down and/or determines a hypotension risk index of the person (30). The fall detector (200) activates the second operating mode if the dwell time exceeds a time threshold and/or if the hypotension risk index exceeds a risk index threshold.

18 Claims, 2 Drawing Sheets

(52) U.S. Cl.
CPC ....... *A61B 2503/08* (2013.01); *A61B 2505/07* (2013.01); *A61B 2562/0204* (2013.01)

(56) References Cited

U.S. PATENT DOCUMENTS

2020/0163590 A1* 5/2020 Lin ........................ A61B 5/1117
2023/0000396 A1* 1/2023 Coffey .................. A61B 5/1117
2024/0054879 A1 2/2024 Krajnc et al.

FOREIGN PATENT DOCUMENTS

WO 2021180049 A1 9/2021
WO 2022096381 A1 5/2022
WO 2022179948 A1 9/2022

OTHER PUBLICATIONS

Rapp, Kilian, et al., "Epidemiology of Falls in Residential Aged Care: Analysis of More Than 70,000 Falls From Residents of Bavarian Nursing Homes," Jamda 13, 2012 (6 Pages).

* cited by examiner

FALL DETECTION SYSTEM FOR FALL DETECTION OF A PERSON, METHOD FOR FALL DETECTION OF A PERSON AND A COMPUTER PROGRAM PRODUCT FOR FALL DETECTION OF A PERSON

CROSS-REFERENCE TO PRIOR APPLICATIONS

This application is the U.S. National Phase application under 35 U.S.C. § 371 of International Application No. PCT/EP2023/074242, filed on Sep. 5, 2023, which claims the benefit of U.S. Provisional Patent Application No. 63/405,557, filed on Sep. 12, 2022 and European Patent Application Ser. No. 22/196,264.0, filed on Sep. 19, 2022. These applications are hereby incorporated by reference herein.

FIELD OF THE INVENTION

The invention relates to a fall detection system for fall detection of a person in a sensing area, method for fall detection of a person in a sensing area and a computer program product for fall detection of a person in a sensing area.

BACKGROUND OF THE INVENTION

For elderly persons (people over 65 years) the leading cause of injuries are falls. The falling down of elderly persons are particularly dangerous as it can lead to broken bones and head injuries. The falling down of an elderly person can in particular be dangerous if the person is living alone as the injury might be so severe that the elderly person is no longer able to help himself or call for help.

This importance of this problem will further increase in importance over the coming decade as many elderly people want to stay in their own home as long as possible. However, the risk of falling and injury for elderly people even in a normal home environment is high. In order to prevent falls and avoid a further increase of the severity of the injuries from the fall, it is important to monitor the activity of elderly persons and in particular to reliably and fast detect if a a fall or injury has occurred.

The most important fall events of elderly people are trip and fall event (a fast fall from the walking position to ground), a fall event when entering a chair and exiting a chair (a fast fall from the sitting position to ground), a soft fall event (person managed to grab a furniture piece to slow the fall to the floor), a brain stroke fall event (slow fall from standing position first to one knee and subsequently down to the ground) and picking something up from the floor fall event (very prolonged fall occurring when elderly person tries to pick something up from the floor and does not have the power to get up again and slowly falls to ground).

US 2019/0175074 A1 discloses a fall detection method, device, and system for detecting whether a target object falls in a detection area. The fall detection method includes: receiving a WIFI signal transmitted by a transmitter in the detection area and extracting CSI data from the WIFI signal, preprocessing the CSI data to obtain CSI data to be identified, and processing the CSI data to be identified to determine a CSI phase difference. A fall is detected based on the CSI phase difference.

SUMMARY OF THE INVENTION

It is an object of the invention to provide a fall detection of a person in a sensing area which is more precise.

According to a first aspect of the present invention, a fall detection system for performing a fall detection of at least one person in a sensing area is provided. The system comprises at least one motion and/or presence detector to detect a motion or a presence of a person. The at least one motion and/or presence detector can be operated in at least a first operating mode with first operating parameters and a second operating mode with second operating parameters. The fall detector detects a position or a presence of the person in the sensing area based on sensing signals from at least one motion and/or presence detector. The fall detector can be operated in the first or second operating mode. The fall detector determines a fall risk be detecting a dwell time a person sitting or lying down and/or by determining a hypotension risk index of the person. The fall detector is configured to activate the second operating mode if an increased fall risk is determined as the dwell time exceeds a time threshold and/or as the hypotension risk index exceeds a risk index threshold.

The fall detector can first determine a fall risk based on the dwell time and/or based on the hypotension risk index. If the fall risk is low or below a threshold, the motion detector and the fall detector can be operated in the first operating mode, which can be a normal operating mode. If the fall risk is high or above a threshold, the motion detector and the fall detector can be operated in the second operating mode, which can be a fall detection operating mode with an increased fall detection sensitivity. The second operating mode can thus be more suitable for fall detection. The second operating mode can be focused on fall detection while other considerations towards e.g. bandwidth use, power consumption etc are of lower importance.

The at least one motion and/or presence detector can be implemented as a network of network devices configured to perform a RF-based sensing in a sensing area. The network devices are distributed in the sensing area and are configured to communicate with each other based on RF signals. At least one network device is configured to receive RF signal from other network devices based on which motion detection or presence detection can be performed.

According to an example, the system comprises a network of network devices and a fall detector. The network devices are distributed in the sensing area and area configured to communicate with each other based on RF signals. At least one network device is configured to receive RF signals which have been transmitted by one network device and have travelled through the sensing area and to output sensing signals based on the received RF signals. A motion detection can be performed based on the sensing signals from the received time-series sensing signals. The fall detector is configured to detect a position and/or posture and/or movement of the person in the sensing area based on the sensing signals from the at least one network device. The fall detector can analyze the sensing signals from the network device to determine whether a person in the sensing area is in a sitting position (e.g. is sitting on a seating, chair or the like) and to determine a sitting time or dwell time, i.e. to determine how long the person is in the sitting position. Similarly, for person lying on the bed. The fall detector can be configured to control the operation of the network devices for a motion detection. In particular, the system and the network devices can have at least a first and second detection mode. The first detection mode can correspond to a normal detection mode. The second detection mode can correspond to a detection mode with an increased sensitivity. The second mode can be activated if the fall detector has determined that the person is in a sitting position (e. g sitting on the chair) in the sensing area for a time period which exceeds a threshold value. In particular, if elderly persons are sitting for a prolonged period on a seating or chair, the danger of falling when exiting a chair is higher. In this case, the sensitivity of the fall detection can be increased.

The fall detector can further be configured to determine a hypotension risk index. The fall detector can activate the second operating mode if the hypotension risk index exceeds a threshold. As an example, if the person is standing up or sitting up suddenly, the hypotension risk is increased. If an elderly person gets out of bed slowly, the hypotension risk is decreased versus the situation where the elderly person is getting up immediately. The fall detector can be configured to detect a recent behavior of the elderly person which may lead to the indication that he can have a higher willingness to take a risk, the hypotension risk index is increased, as due to higher willingness to take risk the elderly may against the recommendation of the caretaker suddenly stand up or sit up. A higher willingness to take risk can be inferred if for instance the elderly is agitated about something. The agitation level can be determined for instance based on the elderly's gestures, the heart beat, and/or the breathing rate. The RF based sensing of the network devices e.g. as described with reference to FIG. 3 can be used to determine the gestures, heart rate and/or breathing rate.

The hypotension risk index is decreased if the fall detector has detected that the elderly person has exercised gently before getting up (like moving the feet up and down and clench and unclench the hands. The hypotension risk index is also decreased if an elderly person has marched in place after standing up. The hypotension risk index can be decreased if the elderly person was sleeping with a raised head (for example by using extra pillows). The hypotension risk index can be increased if an elderly person has a large meal or alcohol or is ill. The hypotension risk index is increased during exercise or when straining on the toilet. The hypotension risk index can be increased if the fall detector has detected based on the sensing signal from the network devices that the elderly person is anxious or is in panic. The hypotension risk index can be increased if the elderly person has taken a hot bath of has showered for a prolonged time. The hypotension risk index can be increased in the morning hours as postural hypotension happens more in the morning when the blood pressure is naturally lower.

The fall detector can be configured to compare the hypotension risk index with a threshold and to activate the second operation mode (fall from chair mode) if the threshold has been exceeded.

According to an example, in the second operation mode (fall of chair mode), the fall detector can be configured to distinguish between four main phases for a sit-to-stand transition, namely flexion (leaning forward), momentum transfer (seat off), extension (returning to the upright position) and stabilization phase. The fall detector is configured to compare the motion detected during these four phases. If the detected motion does not correspond to the four phases, the fall detector can indicate in an alert that a near fall or a fall from the seating or chair is possible. Alternatively, upon inferring from the sit-to-stand transition an elevated fall risk, the fall detector may enter a third fall detection mode which maximally prioritizes the accuracy of the fall detection over other considerations such as wireless bandwidth and energy consumption of the radio.

According to an example, the fall detector is configured to analyze the sensing signals from the network devices during the four phases during the sit to stand transition and to detect a regular motion trail across the room after the person has been getting up from the chair. If the motion which the elderly person has performed corresponds to a walking motion, then no alert is sounded. If, however, no walking motion is detected, the alert can be issued. This approach can for instance even catch hard-to-detect fall types such as the elderly-after getting up —-again falling back on the chair and sliding off the chair.

The fall detector is also configured to take a high potential risk index into consideration when selecting the operation mode of the fall detection system. The high potential risk index can be determined by the fall detector by analyzing the motion of the person before he has sat down on the chair, during the time period he is sitting down on the chair and/or right after the person has got up.

The fall detector is configured to at least partially control the network devices of the network. In particular, the network devices of the network can be operated in at least a first and second operating mode. The first operating mode may correspond to a normal operating mode. The second operating mode may correspond to an enhanced fall detection mode. In the fall detection mode, the network devices which are transmitting the RF signals can be operated with an increased power. Furthermore, the transmitting network devices may operate at different frequencies. Moreover, in the second operating mode, namely the fall detection operating mode, some of the network devices arranged in the sensing area can be chosen to perform the motion detection. For instance, the number of network devices participating in the fall detection may be increased from two devices to all five network devices in the room Moreover, in the second operating mode, namely the fall detection operating mode, the network devices may transmit RF signals more frequently, for instance instead of 500 Hz, the network device may transmit RF signals for fall detection at 1500 Hz.

If the transmitting power is increased, this could lead to an increased value and/or signal-noise ratio of the signal quality matrix (RSSI, CSI) used as input for the fall detection algorithm. This may lead to a higher resolution and better inferences (e.g. fewer false positives or false negatives) for the fall detection algorithm.

In the fall detection operating mode, the transmission beam of the transmitting network devices can be altered.

The network of network devices which can also be understood as a sensing network comprises at least two network devices. Preferably, the network comprises more than three network devices, wherein the number of network devices in the network can be adapted based on the sensing area (fall detection area) in which a sensing (fall detection) should take place. For example, the larger the space the more network devices can be provided in the network and/or the more complex a shape of the space the more network devices can be provided in the network.

In an example, the status and/or position and/or posture is determined based on i) the signal strength of the plurality of detected sensing signals and/or based on ii) channel state information derived from the plurality of detected sensing signals and the predetermined generated wireless sensing signal transmitted by the wireless transmitter. A status and/or position and/or posture of at least one subject in the sensing area can be based on the signal strength of the plurality of detected sensing signals. Since a signal strength of the sensing signal depends on an amplitude of the wireless signal that directly or indirectly (via reflections/diffraction) reaches the wireless receiver, the single strength is indicative of the different paths the wireless signal can travel from the wireless transmitter to the wireless receiver. Since these paths are highly dependent on the environment between the transmitting network device and the receiving network device and thus also dependent on the position of subjects in the environment, the signal strength is indicative of these positions. Moreover, since the signal strength of a plurality of detected sensing signals is utilized, and as the sensing signals are detected by network devices arranged at different locations, more precise information on the environment of the network devices can be obtained as a plurality of different wireless multipaths in the sensing area.

Furthermore, the position of at least one subject in the sensing area can be based on channel state information derived from the plurality of detected sensing signals and the predetermined generated wireless signal emitted by the transmitting network devices The channel state information is indicative of the properties of a path that the wireless signal has taken from the wireless transmitter in the first network device to the wireless receiver in the second network device and thus describes how the wireless signal has propagated from the first network device (transmitter) to the second network device (receiver). Accordingly, the channel state information is also indicative of an interaction of the wireless signal with the subject along the propagation path. Thus, the channel state information provides very accurate information on the environment of the network with which the wireless signal has interacted, for instance, from which it has been reflected, scattered or absorbed. Since the predetermined generated wireless signal of the first network device is known and due to the network characteristics of the network, the channel state information can be derived from the sensing signals and the predetermined generated wireless signal.

According to an example, the network devices can be implemented as light (ceiling light, desk lamp), as smart device (smartphone, smart watch, tablet, smart speaker) or as network capable electronic device (e.g. laptop).

In an example, at least one of the network devices comprises a lighting unit to implement a lighting functionality. However, in other examples the network devices can also comprise other functionalities like entertainment functionalities, monitoring functionalities, etc.

In an example the motion and/or presence detector is implemented as radar sensor (e.g. WiFi-based radar sensing, FMCW radar-based sensing, Impulse UWB radar-based sensing or as a ToF (Time of Flight)-based sensor. The radar sensor or the time-of-flight sensor can be operated in at least a first and second operating mode. The first operating mode can be a normal operating mode and the second operating mode can be a fall detecting operating mode e.g. with an increased sensitivity. The fall detector detects a position or a presence of the person in the sensing area based on sensing signals from at least one motion and/or presence detector. The fall detector detects a dwell time a person sitting or lying down and/or determines a hypotension risk index of the person. The fall detector is configured to activate the second operating mode if the dwell time exceeds a time threshold and/or if the hypotension risk index exceeds a risk index threshold.

The fall detector can be implemented as a dedicated device or can be integrated in a wireless hub or central control unit. Alternatively, the fall detection may also be performed by one of the network devices. Alternatively, the fall detection may be performed by a remote device like a server in the cloud. Furthermore, the fall detection may be performed by an internet-of-things IoT edge device. Therefore, the position where the fall detection is performed is not relevant as long as the function is performed based on the signals detected by the network devices.

In another aspect of the invention, a computer program product for performing fall detection of a person is presented, wherein the computer program product comprises program code means for causing the system as described above to execute the method as described above.

It shall be understood that the system, the method, the computer program, and the network comprising this system, have similar and/or identical preferred examples or embodiments, in particular, as defined in the dependent claims.

It shall be understood that a preferred embodiment of the present invention can also be any combination of the dependent claims or above embodiments with the respective independent claim.

It shall be understood that the aspects described above and specifically the system of claim 1, the method of claim 11 and the computer program product of claim 13 have similar and/or identical preferred embodiments, in particular as defined in the dependent claims.

These and other aspects of the invention will be apparent from and elucidated with reference to the embodiments described hereinafter.

DETAILED DESCRIPTION OF EMBODIMENTS

Figure 1:
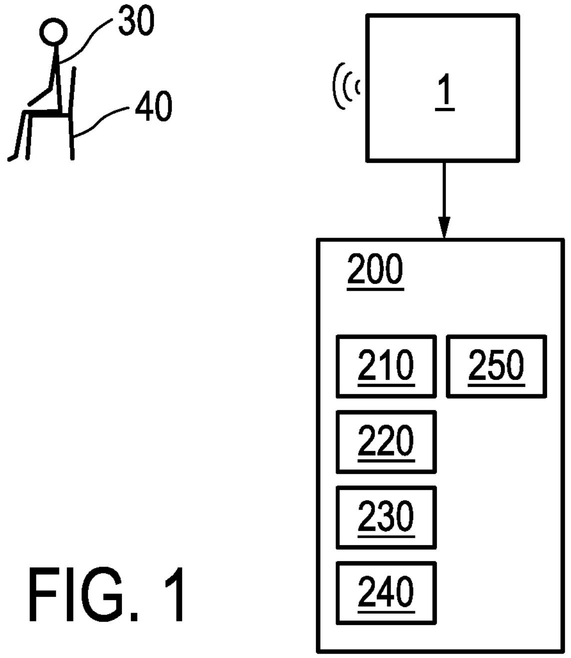
FIG. 1 shows a block diagram of a fall detection system for performing a fall detection of a person in a sensing area.

FIG. 1 shows a block diagram of a fall detection system for performing a fall detection of a person in a sensing area. The fall detection system 2 comprises a motion and/or presence detector 1, which can detect a motion or a presence of a person 30 in a sensing area 20. The fall detection system 2 also comprises a fall detector 200.

The fall detector 200 comprises a controller 210, optionally a memory 220 and a motion analyzer 230. The motion analyzer 230 can be implemented as a posture detector or a presence detector. The sensing signals from the motion and/or presence detector can be used by the motion analyzer to detect the presence of a static person (who is not moving) as the presence of the human body mass will alter the wireless multipath of the signals detected by the motion and/or presence detector.

The controller 210 can control the operation of the motion and/or presence detector 1. The motion and/or presence detector 1 can be operated in at least a first and second operating mode. The controller 210 can initiate at least a first and second operating mode. The first operating mode being a normal operating mode. The second operating mode being a fall detection operating mode in particular with an increase sensitivity. The controller 210 of the fall detector 200 can change the operation of the motion detector and/or presence detector 1 as compared to the first operating mode. The controller 210 can be able to change parameters of the motion and/or presence detector 1 like the transmission power, the frequency of the transmission, and the wireless messages sent per second.

The fall position detector 200 may also comprise an alert unit 250 for initiating an alert if a fall is detected.

The memory 220 of the fall detector 200 can be used to store historical data, which can be used for further analysis. Optionally, the memory 220 can also be used to store user specific settings or parameters. Such user specific parameters can relate to the age of a user, the health of the user, etc.

The motion analyzer 230 receives the sensing signals from the motion and/or presence detector 1 and performs a motion/presence analyses of a person 30 in the sensing area 20, in particular of a person 30 in a sitting position (e.g. sitting on a seating like a chair 40 or something similar). The motion analyzer 230 can in particular determine a sitting time or dwell time of the person 30 on the seating 40. The motion analyzer 230 can also determine a dwell time of the person 30 lying in bed or on a sofa or the like. In other words, the motion analyzer 230 can determine a time period of inactivity of the user. This parameter can then be used by the fall detector 200 (for example by the controller 210 or the motion analyzer 230) to select one of the at least two operating modes. For example, if the time period of inactivity, like the dwelling time of the person 30 on the seating 40 or lying down exceeds a threshold, the second operating mode is activated. Similarly, the motion analyzer 230 may additionally also perform vital sign detection (heartbeat rate, breathing rate) to further improve its decision when to activate the second operating mode. For instance, if the period of inactivity is accompanied by a very low heart rate, the risk of fall further increases.

In the second operating mode, the operating parameters of the motion and/or presence detectors 1 is changed as compared to the first operating mode. These changes are performed in order to improve the sensitivity of the fall detection. In particular, the second operating mode is tuned to achieve an improved fall detection for a situation when a person 30 is getting up from the seating40 or is getting up after having lied down. While trip-and-fall-type falls are relatively easily to detect by the fall detector as the person first walks and then falls hard to ground and the walking trajectory stops, getting-up-from-the-chair-type falls generate a much less distinct time-series RSSI/CSI characteristics. Accordingly, thanks to the second operation mode utilizing a more advanced motion sensing, e.g. a fall off chair detection is achieved. The second operating mode can also refer to a chair fall mode.

The fall detector 200 can optionally comprise risk analyzer 240. The risk analyzer 240 serves to detect and analyze a high potential risk index. If the high potential risk index HRI is high, then this information can be used by the controller 210 to select the second operating mode. The second operating mode can correspond to a special high-performance sensing mode to optimally capture falls from chair/falls after a few steps from the chair for example due to light headedness.

The motion and/or presence detector can be implemented as a network of network devices as described with reference to FIG. 3, as radar sensors (e.g. FMCW radar, Impulse UWB radar-based sensing), as thermal sensors, as a time-of-flight sensor or as sound sensors. These can be used to detect a motion and/or presence of a person in a sensing area. They can be used to determined a dwell time of a person on a seating or while lying down. In other words, they are used to determine a period of inactivity which could influence a risk of falling down when the period of inactivity has ended and the person starts to move, i.e. get up or stands up.

Figure 2:
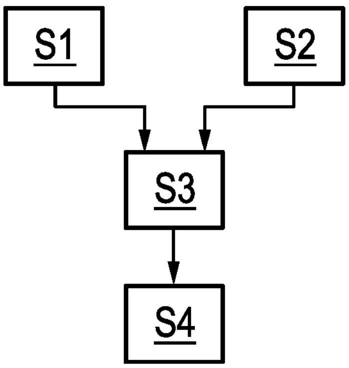
FIG. 2 shows a flow chart of a fall detection.

FIG. 2 shows a flow chart of a fall detection. The fall detection can be performed by a fall detection system 2 as described with reference to FIG. 1. In step S1 a motion and/or presence detection is performed. In step S2 a risk analysis is performed. In step S3 the fall detector 200 analyses the motion and/or presence detection results. Furthermore, the fall detector can optionally analyze the results of the risk analysis. In step S4, the fall detector 200 activates the second operating mode if the dwell time exceeds a time threshold and/or the risk index exceeds as risk threshold.

Figure 3:
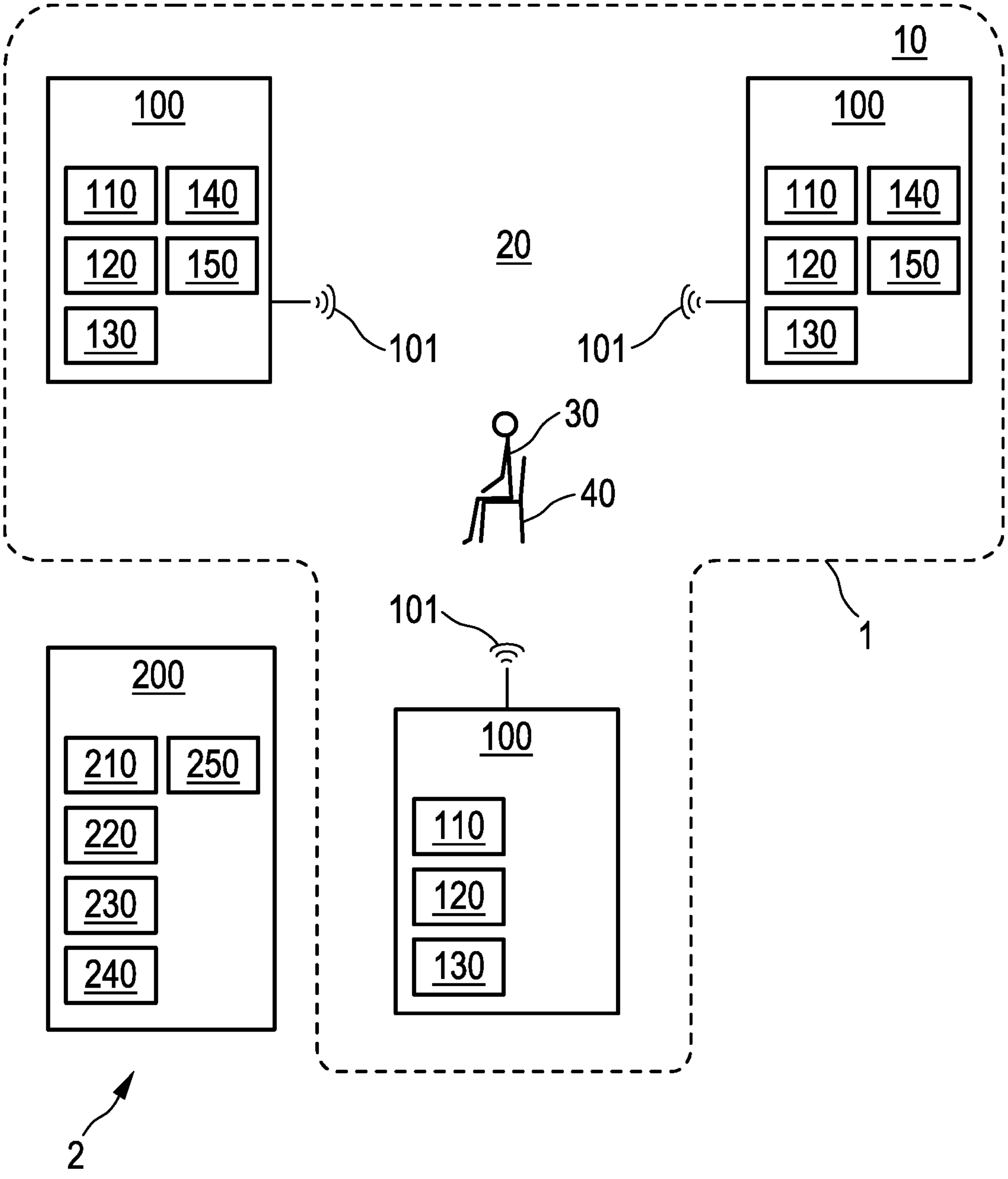
FIG. 3 shows a block diagram of a fall detection system.

FIG. 3 shows a block diagram of a fall detection system for performing a fall detection of a person in a sensing area. The fall detection system 2 comprises a motion and/or presence detector 1. The motion and/or presence detector 1 comprises a network 10 of preferably several network devices 100. In other words, the motion and/or presence detector 1 can be implemented as a network 10 of several network devices 100. The fall detection system 2 comprises at least one fall detector 200 for detecting a fall of a person 30 in a sensing area 20. The network devices 100 are able to communicate with each other based on RF signals. A network device 100 comprises an RF transceiver or an RF transmitter 110 as well as an RF receiver for the RF communication. The network device 100 can optionally comprise a lighting unit 120. Furthermore, a network device may comprise a controller 130.

According to an example, a network device 100 can comprise a sound generator 140 and/or a sound sensor 150. The network device can optionally comprise either the sound generator 140, the sound sensor 150 or both. The sound generator 140 and the sound sensor 150 will only be provided if at least part of the motion sensing is to be performed based on sound signals. Otherwise, the sound generator 140 and the sound sensor 140 can be omitted.

The network devices 100 can be arranged at different positions in a sensing area 20. In the sensing area, a person 30 can for example sit on a seating like a chair 40.

The fall detector 200 comprises a controller 210, optionally a memory 220 and a motion analyzer 230 and/or a posture detector and/or a true presence detector. The motion analyzer 230 can be implemented as a posture detector or a presence detector. The RF sensing can be used by the presence detector to detect the presence of a static person (who is not moving) as the presence of the human body mass will alter the wireless multipath in the sensing area.

The controller 210 can control the operation of at least one of the network devices 100. The controller 210 can initiate at least a first and second operating mode. The first operating mode being a normal operating mode. The second operating mode being a detecting-a-fall-off=chair operating mode, i.e. in the second operating mode, the controller 210 of the fall detector 200 can change the operation of the at least one network device 100 as compared to the first operating mode. The controller 210 can be able to change parameters of the network devices 100 like the transmission power, the frequency of the RF transmission, the wireless messages sent per second. Furthermore, the controller 210 can be able to select some of the plurality of network devices. Accordingly, only selected ones of the network devices 100 are used to detect RF signals which have been transmitted by at least one of the network devices 100.

The fall position detector 200 may also comprise an alert unit 250 for initiating an alert if a fall is detected.

The memory 220 of the fall detector 200 can be used to store historical data, which can be used for further analysis. Optionally, the memory can also be used to store user specific settings or parameters. Such user specific parameters can relate to the age of a user, the health of the user, etc.

The motion analyzer 230 receives the sensing signals from the network devices 100 and performs a motion analyses of a person 30 in the sensing area 20, in particular of a person 30 in a sitting position (e.g. sitting on a chair 40 or something similar). The motion analyzer 230 can in particular determine a sitting time or dwell time of the person 30 in a sitting position, like on the chair 40. This parameter can then be used by the fall detector 200 (for example by the controller 210 or the motion analyzer 230) to select one of the at least two operating modes. For example, if the dwelling time or sitting time of the person 30 in a sitting position (e.g. sitting on a seating or chair 40) exceeds a threshold, the second operating mode is activated.

In the second operating mode, the operating parameters of the transmitting and/or receiving network devices are changed as compared to the first operating mode. These changes are performed in order to improve the sensitivity of the fall detection. In particular, the second operating mode is tuned to achieve an improved fall detection for a situation when a person 30 is getting up from the chair 40. While trip-and-fall-type falls are relatively easily to detect by the fall detector as the person first walks and then falls hard to ground and the walking trajectory stops, getting-up-from-the-chair-type falls generate a much less distinct time-series RSSI/CSI characteristics. Accordingly, thanks to the second operation mode utilizing a more advanced RF sensing, a fall off chair detection is achieved. The second operating mode can also refer to a chair fall mode.

The fall detector 200 can optionally comprise risk analyzer 240. The risk analyzer 240 serves to detect and analyze a high potential risk index. If the high potential risk index HRI is high, then this information can be used by the controller 210 to select the second operating mode. The second operating mode can correspond to a special high-performance sensing mode to optimally capture falls from chair/falls after a few steps from the chair for example due to light headedness. The second operating mode can have a different assignment of the RF sensing modes, namely the RF network devices. Furthermore, the transmit power may be different, the transmit/receive beam angles can be different or the signal processing of the CSI signals may be different.

In the second operating mode, the activated or active network devices 100 may be different as in the first operating mode. Optionally, during the configuration of the fall detection system, the position of a chair 40 in the room may be determined beforehand and can be for example stored in the memory 220. Accordingly, in the second operating mode, the position of the chair 40 may be taken into consideration when choosing those network devices 100 from the plurality of network devices 100 which should be used during the fall detection.

The controller 210 can activate the second operating mode (a chair fall mode) if the sitting time or dwell time of an elderly on a chair has exceeded a threshold and/or if the high potential risk index HRI is high. Also a combination of these two parameters can be used by the controller 210 to activate the second operating mode.

The high potential risk index HRI can be considered high when the person is standing up or sitting up suddenly, when a person is getting up out of bed suddenly or when recent behavior of the person indicates that he has a higher willingness for risk taking. If the person had a large meal or alcohol or is ill, the high potential risk index can be increased. Moreover, during exercise or when straining on the toilet, the high potential index can also be increased. Furthermore, if the system has detected that the person is anxious or may be panicking, the high potential risk index is increased. Furthermore, if the person has taken hot baths or showers for a prolonged time, the high potential index is also increased. During the morning hours, the high potential risk index is also increased.

The high potential risk index HRI can be decreased or lowered when the person is getting out of bed slowly, when the person is exercising gently before getting up, when the person is marching in placed after standing up, when the person is sleeping with a raised head (for example with extra pillows).

A threshold may be associated with the high potential risk index. If the high potential risk index exceeds this threshold, the controller can activate the second operating mode. On the other hand, if the high potential risk index is below or far below the threshold, the controller may not activate the second operating mode.

The motion analyzer 230 can analyze a motion of the person when standing up. In particular, the motion analyzer can analyze four motion phases during a sit-to-stand transition, namely flexion (leaning forward), momentum transfer (seat-off), extension (returning to upward position) and the stabilization phase. The motion analyzer 230 and/or the risk analyzer 240 can analyze the motion of the user during the sit-to-stand transition. If a user does not follow these four motion phases, the motion analyzer 230 or the risk analyzer 240 can indicate this fact to the controller 210 such that the controller 210 can activate the second operating mode.

In the second operating mode, the transmission power of the transmitting network devices can be increased to increase the sensitivity of the system. Alternatively or in combination, the transmission beam can be adapted. Here, the beam can be narrowed or the main direction of the transmission can be changed. A combination thereof is also possible. An adaptation of the transmission beam can allow a confinement of the sensing volume. This is advantageous as it can be less prone to interferences from other objects. One example can be a ceiling mounted pedal fan or a further person or pet in the room. The motion or movement of the pedal fan or the second person or a pet can influence the detection of the motion of the person getting up from the chair.

In addition or alternatively, the number of network devices which are transmitting and/or receiving the transmitted signals can be increased to increase the coverage of the system. Accordingly, as the number of network devices is increased, the density of the transmitted RF signals can be increased which in turn increases the sensitivity of the signal and increases the signal to noise ratio.

In addition or alternatively, from the plurality of network devices, at least one or more network devices for transmitting the RF signals can be selected. Hereby, the sensing topology can be changed for example depending on the location of the chair and thus the expected future fall event.

According to an example, the operation of the receiving network devices can also be changed. In particular, the reception volume can be modified. The reception volume may indicate the region or space where signals are receivable with the required signal quality (RSSI, CSI). In addition or alternatively, beam shaping can be performed at the receiving network device.

The fall detector 200 can also be able to be able to store user parameters or settings. Such settings can be the dehydration of a person, vitamin B12 deficiency, alcohol consumption, drugs and medications, lower body weaknesses.

Preferably, at least two network devices 100 are used for the fall detection.

According to an embodiment, the network devices 100 can be implemented as ceiling lights.

A network device according to an example can be regarded as any device adapted to form a network with other network devices. In particular, a network device comprises a network device communicator that is adapted to receive and transmit wired or wireless signals, for instance, radiofrequency signals, infrared signals, transmit and receive audio signals for audio sensing purposes, electrical signals, etc.

The network between the network devices can then be formed through a communication between the network devices following a known network communication protocol like WiFi, ZigBee, Thread, Bluetooth, etc. Preferably, the network devices refer to smart devices, i.e. devices comprising a communication unit for receiving and transmitting network communication signals but which otherwise fulfil the function of a corresponding conventional device. In particular, such a smart device can be a smart home or office device, in which case the corresponding conventional function would be that of a conventional home or office device. Preferably, the conventional function refers to a lighting function and the network devices refer to network lighting devices that are further adapted to comprise a wireless transmitter and/or a wireless receiver. Optionally the network devices can also comprise a sound generator and/or a sound detector for audio sensing. However, the network devices can also refer, for instance, to smart plugs, smart switches, etc.

The system can be part of the network, for instance, can be part of one or more of the network devices. In particular, the system can be provided as hard- and/or software as part of one of the network devices or distributed over a plurality of the network devices that are in communication with each other to form the system. However, the system can also be provided as a standalone system, for instance, in a device that is not part of the network of network devices but is directly or indirectly in communication with at least one of the network devices, for instance, to control the network devices. For instance, the system can be provided as part of a handheld computational device like a smartphone, a tablet computer, a laptop etc. However, the system can also be located in a cloud formed by one or more servers, wherein in this case the system might communicate with the network, in particular, the network devices, via one or more devices that are connected to the cloud like a router.

According to an example, a network 10 with a plurality of network devices 100 implemented as lighting or luminare devices can be provided. The network devices 100 comprise microphones (sound sensors 130) and/or speakers (sound generators 120). Therefore, the sound generators 120 and the sound sensors 130 can be distributed among a sensing area 20.

The fall detector 200 can be implemented as a dedicated device or can be integrated in a wireless hub or central control unit. Alternatively, the fall detection 200 may also be performed by one of the network devices 100. Alternatively, the fall detection may be performed by a remote device like a server in the cloud. Furthermore, the fall detection may be performed by an internet-of-things IoT edge device. Therefore, the position where the fall position detection is performed is not relevant as long as the function is performed based on the signals detected by the network devices.

Moreover, the fall detection may also be performed by a smart device which can be positioned in the sensing area and which can communicate with the network 10 and the network devices 100. As an example, an application may be running on such a smart device which is performing the fall position detection. Alternatively, the fall detection may be performed by a smart speaker or a smart watch which can be arranged in the sensing area 20.

According to an example, several network devices 100 are arranged in the sensing area 20. A first plurality of network devices 100 may be arranged in the vicinity of a person 30. A second plurality of network devices 100 may be arranged further away from the first plurality of network devices 100. In order to improve the accuracy of the fall detecting, the fall position detector 200 may select some of the first plurality of network devices 100.

According to a further exapmle, the information from the fall detection may be used during an RF position or motion sensing. According to an example, if based on the fall detection it is detected that a person has fallen from the chair, the sensing arrangement may be reconfigured and those network devices 100 are chosen which have a direct line of sight to the chest area of the person which might have fallen from the chair in order to more accurately measure the vital signs of the person. The vital signs measurement can be performed based on audio sensing or RF sensing.

In an example a network device 100 can placed on the desk and can be implemented as a table lamp (the network device may also comprise a light unit 140). Moreover, a network device 100 can be implemented as a ceiling network devices 100. The network device 100 can be arranged in or at the ceiling.

According to an example, the fall detector 200 controls a number of network devices 100 arranged in the sensing area 20 (for example at the ceiling) to perform the fall detection.

According to an example, it is proposed to preferably use a lighting system as detecting units distributed across the room to monitor a subject status and/or position. According to an example, the network devices may be part of a lighting system and can each comprise at least one light unit.

According to an example, a number of network devices (sensing nodes) can be provided.

According to an example, a network device 100 can comprise a sound generator 140 and/or a sound sensor 150. The network device can optionally comprise either the sound generator 140, the sound sensor 150 or both.

Hence, the motion and/or presence detector can be implemented by a sound generator and a sound sensor. In other words, the motion and/or presence detection is performed using a sound signal. Optionally, the sound generator and the sound sensor can be part of a network device as described with reference to FIG. 3. Hence, the status and/or position and/or posture can be determined based on the signal strength of the plurality of detected sensing signals (audio signals) and/or based on channel state information derived from the plurality of detected sensing signals (audio signals). A status and/or position and/or posture of at least one subject in the sensing area can be based on the signal strength of the plurality of detected sensing signals. Since a signal strength of the sensing signal depends on an amplitude of the sound that directly or indirectly (via reflections/diffraction) reaches the sound detector, the single strength is indicative of the different paths the sound can travel from the sound generator to the sound sensor. Since these paths are highly dependent on the environment between the sound generator and the sound detector and thus also dependent on the position of subjects in the environment, the signal strength is indicative of these positions. Moreover, since the signal strength of a plurality of detected sensing signals is utilized, wherein the sensing signals result from the detection of sound detectors arranged at different locations, information on the environment of the network devices from a plurality of different sound paths is provided by the sensing signals.

Moreover, the position of at least one subject in the sensing area can be based on channel state information derived from the plurality of detected sensing signals and the predetermined generated sound. The channel state information is indicative of the properties of a path that the sound has taken from the sound generator to the sound detector and thus describes how the sound has propagated from the sound generator to the sound detector. Accordingly, the channel state information is also indicative of an interaction of the sound with the subject along the propagation path. Thus, the channel state information provides very accurate information on the environment of the network with which the sound has interacted, for instance, from which it has been reflected, scattered or absorbed. Since the predetermined generated wireless signal of the first network device is known and due to the network characteristics of the network, the channel state information can be derived from the sensing signals and the predetermined generated sound.

Other variations to the disclosed examples or embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A fall detection system for performing a fall detection of at least one person in a sensing area, comprising:

at least one motion or presence detector configured to detect a motion or a presence of a person, the at least one motion or presence detector is operated in at least a first operating mode with first operating parameters or a second operating mode with second operating parameters, and a fall detector configured to detect a position or a presence of the person in the sensing area based on a sensing signal from the at least one motion or presence detector in the first or second operating mode, wherein the at least one motion or presence detector has a network of network devices configured to perform an RF-based sensing in the sensing area, the network devices are distributed in the sensing area and are configured to communicate with each other based on RF signals, and the network devices are further configured to:

generate an RF signal by at least one transmitting network device of the network devices, detect the RF signal, by at least one receiving network device of the network devices that is different from the at least one transmitting network device, after the RF signal has propagated from the at least one transmitting network device through at least a portion of the sensing area to the at least one receiving network device, and generate, by the at least one receiving network device, the sensing signal indicative of the detected RF signal, and wherein the fall detector is further configured to:

detect, based on the sensing signal, a dwell time during which the person is in a seated position or a lying position, activate the second operating mode in response to the dwell time exceeding a time threshold, wherein in the second operating mode a number of the network devices participating in the RF-based sensing is increased relative to the first operating mode, detect a fall of the person while operating in the second operating mode based on the sensing signal from the at least one receiving network device, and in response to detecting the fall of the person, reconfigure the network of network devices by selecting a subset of the network devices, and to measure at least one vital sign of the person based on a sensing signal received from the selected subset of the network devices.

2. The system according to claim 1, wherein at least one receiving network device of the network devices is configured to receive RF signals from other network devices and to generate, based on the received RF signals, a sensing signal usable by the fall detector to perform at least one of motion detection, presence detection, or vital sign detection.

3. The system according to claim 2, wherein the fall detector comprises a controller which is configured to control the operation of at least one of the network devices to perform the RF-based sensing in the sensing area.

4. The system according to claim 2, wherein the fall detector is configured to detect, based on the sensing signal, a motion of the person when the person is standing up from a sitting position or is getting up from a lying position, wherein the fall detector is configured to compare the detected motion with a standard sit-to-stand transition motion or a standard lying-to-stand transition motion, wherein the fall detector is configured to issue an alert if the detected motion does not correspond to the standard sit-to-stand transition motion or the standard lying-to-stand transition motion.

5. The system according to claim 1, wherein the second operating parameters of the second operating mode have at least one of an increased transmission power of the RF signal, a change of a transmission frequency of the RF signal, and a modification of a reception volume of the at least one receiving network device.

6. The system according to claim 2, wherein at least one of the network devices comprises a lighting unit configured to emit visible light.

7. The system according to claim 2, wherein at least one network device is implemented as a light unit selected from the group consisting of a ceiling lamp, a lighting wall switch, a user interface device, and a desk lamp.

8. The system according to claim 2, wherein at least one network device comprises a sound generator and a further network device comprises a sound sensor, wherein the further network device is further configured to output a sound-based sensing signal from the sound sensor for use by the fall detector to perform at least one of motion detection, presence detection, and vital sign detection.

9. The system according to claim 1, wherein the at least one motion or presence detector further comprises at least one of a radar sensor or a Time-of-Flight-based sensor.

10. A method for performing a fall detection of at least one person in a sensing area, comprising the steps of:

detecting a motion or presence of a person by at least one motion or presence detector, wherein the at least one motion or presence detector is operated in at least a first operating mode with first operating parameters or a second operating mode with second operating parameters, detecting a position or a presence of the person in the sensing area by a fall detector based on a sensing signal from the at least one motion or presence detector in the first or second operating mode, wherein the at least one motion or presence detector comprises a network of network devices configured to perform an RF-based sensing in the sensing area, wherein the network devices are distributed in the sensing area and are configured to communicate with each other based on RF signals comprising the steps of:

generating an RF signal by at least one transmitting network device of the network devices, detecting the RF signal by at least one receiving network device of the network devices that is different from the at least one transmitting network device after the RF signal has propagated from the at least one transmitting network device through at least a portion of the sensing area to the at least one receiving network device, generating, by the at least one receiving network device, a sensing signal indicative of the detected RF signal, detecting, by the fall detector and based on the sensing signal, a dwell time during which the person is in a seated position or a lying position, activating, by the fall detector, the second operating mode in response to the dwell time exceeding a time threshold, wherein in the second operating mode a number of the network devices participating in the RF-based sensing is increased relative to the first operating mode, and detecting, by the fall detector, a fall of the person while operating in the second operating mode based on the sensing signal from the at least one receiving network device, in response to detecting the fall of the person, reconfigure the network of network devices by selecting a subset of the network devices, and to measure at least one vital sign of the person based on a sensing signal received from the selected subset of the network devices.

11. A non-transitory computer readable medium having stored thereon instructions for performing the method of claim 10 when run on a processor.

12. The system according to claim 1, wherein the sensing signal is indicative of at least one of (i) a signal strength of the detected RF signal or (ii) channel state information derived from the detected RF signal and the generated RF signal, and wherein the fall detector is further configured to detect at least one of the position, the presence, the dwell time, or the fall of the person based on the signal strength or the channel state information.

13. The system according to claim 1, wherein the second operating parameters further comprise a higher transmission rate of the RF signal by the at least one transmitting network device relative to the first operating parameters.

14. The system according to claim 1, wherein the fall detector is further configured to determine a hypotension risk index of the person based on the sensing signal, and to activate the second operating mode in response to the hypotension risk index exceeding a risk index threshold, independently of whether the dwell time exceeds the time threshold.

15. The system according to claim 1, wherein the subset of the network devices selected by the fall detector in response to detecting the fall of the person has a line of sight to a chest area of the person.

16. The system according to claim 1, wherein the fall detector comprises a memory storing a position of a seat within the sensing area, and wherein in the second operating mode, the fall detector is configured to select, based on the stored position of the seat, a subset of the network devices to participate in the RF-based sensing such that the selected subset differs from a set of network devices used for the RF-based sensing in the first operating mode.

17. The system according to claim 1, wherein the fall detector is further configured to analyze, in the second operating mode, a sit-to-stand transition of the person based on the sensing signal across four motion phases comprising a flexion phase, a momentum-transfer phase, an extension phase, and a stabilization phase, and to issue an alert when a motion of the person across the four motion phases does not correspond to a standard sit-to-stand transition motion.

18. The method according to claim 10, wherein the subset of the network devices selected by the fall detector in response to detecting the fall of the person has a line of sight to a chest area of the person.

* * * * *